United States Patent [19]

Hinchman

[11] 4,157,657

[45] Jun. 12, 1979

[54] PROFILING WATER QUALITY SENSING SYSTEM

[75] Inventor: John H. Hinchman, San Diego, Calif.

[73] Assignee: General Dynamics Electronics Division, San Diego, Calif.

[21] Appl. No.: 841,680

[22] Filed: Oct. 13, 1977

[51] Int. Cl.² .................... G01N 33/18; B66C 23/60
[52] U.S. Cl. ........................................ 73/53; 73/344; 254/139
[58] Field of Search ............. 73/432 R, 170 A, 29 Z, 73/343 R, 344, 345, 425.4 R, 53; 254/139, 173 R; 318/9; 200/61.14, 61.15, 61.16

[56] References Cited

U.S. PATENT DOCUMENTS

| | | | |
|---|---|---|---|
| 2,741,126 | 4/1956 | Anderson et al. | 73/344 |
| 2,756,404 | 7/1956 | Anderson et al. | 73/170 A X |
| 2,927,170 | 3/1960 | Brown | 200/61.14 |
| 3,052,878 | 9/1962 | Berry | 200/61.14 X |
| 3,782,692 | 1/1974 | Casco et al. | 254/139 |
| 3,922,808 | 12/1975 | Rieth et al. | 73/170 A X |
| 4,000,653 | 1/1977 | Booth et al. | 73/343 R |

Primary Examiner—Charles A. Ruehl
Assistant Examiner—Joseph W. Roskos
Attorney, Agent, or Firm—Brown & Martin

[57] ABSTRACT

A system for obtaining a vertical profile of water quality in a body of water is disclosed. The system includes a sensor for sensing predetermined characteristics of water and the depth of water at which the predetermined characteristics are sensed, a cable attached to the sensor for holding the sensor, and a winch assembly attached to the cable for deploying and retrieving the cable and the sensor in a body of water. The winch assembly includes a non-ventilated DC motor coupled to the drum for driving the drum to retrieve the cable, and for generating electricity during deployment of the cable in response to the torque on the motor created by the cable and the sensor during deployment, an electromagnetically released brake coupled to the motor for braking the motor when the brake is not energized, a battery for providing energy for the motor and the brake, and a motor controller coupled to the battery for providing constant voltage excitation of the motor and for controlling the brake. The motor controller includes a circuit which inhibits the motor from operating as a motor during deployment of the cable, and a circuit for reversing the polarity of the motor to cause the motor to generate electricity for recharging the battery during deployment of the cable.

A control circuit is coupled to the sensor and to the motor controller for causing the motor controller to brake and stop the motor in response to sensing a predetermined depth of water.

15 Claims, 13 Drawing Figures

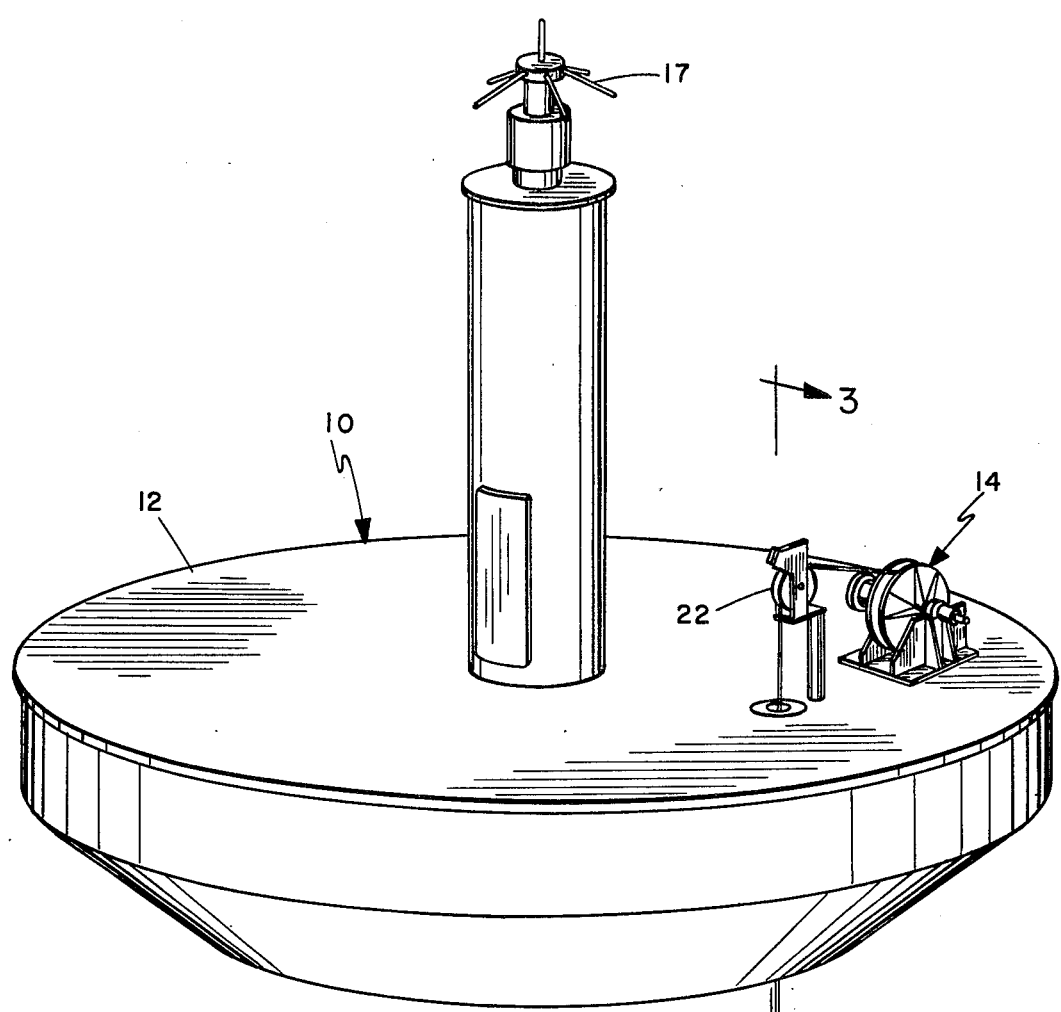
Fig. 1
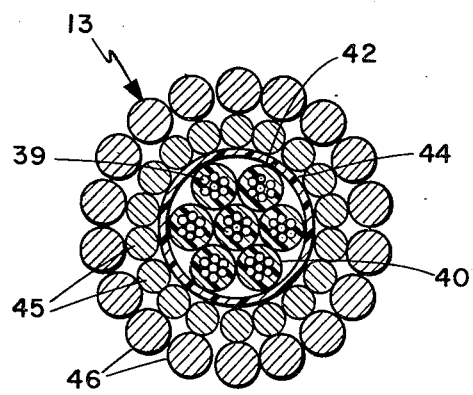
Fig. 7
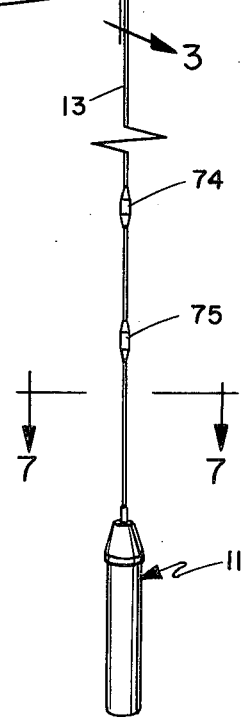

PROFILING WATER QUALITY SENSING SYSTEM

BACKGROUND OF THE INVENTION

The present invention generally pertains to systems for obtaining a vertical profile of water quality in a body of water and is specifically directed to such a system which is capable of long term unattended operation.

In a typical prior art system a sensor for sensing predetermined characteristics of water, such as temperature, conductivity, pH, etc., is attached to a cable and deployed in and retrieved from a body of water by a winch assembly attached to the cable. The winch assembly includes a drum for receiving the cable and a motor that is coupled to the drum for driving the drum to retrieve the cable. The motor typically is an AC motor which is energized by a generator and controlled by a motor controller.

Such a system usually has been operated from a boat and has been attended by personnel during such operation.

It sometimes is desirable to obtain water quality profile measurements from bodies of water over an extended period of time and in locations when manned operation of the system is extremely expensive. Accordingly, it is preferable to be able to provide a water quality profile system which is capable of unattended operation.

A survey of manufacturers of hydrographic winch assemblies has revealed that prior art commercially available winches are unsuited for low energy consumption, long term, unattended operation aboard buoys. In fact, all such prior art commercially available winch assemblies require operator supervision.

A water quality profile measurement system capable of unattended operation was mounted on a buoy and employed by the Scripps Institution of Oceanography, La Jolla, California, some years ago. In the Scripps system the winch assembly included a narrow drum having large flanges for receiving the cable, a lead sheave for guiding the cable to and from the drum, and located a sufficient distance from the drum to enable proper cable spooling on the drum, a DC motor coupled to the drum for driving the drum to retrieve the cable; a worm gear assembly for coupling mechanical power provided by the motor to the drum at a low speed and high torque; a battery for providing energy for the motor and a motor controller coupled to the battery for controlling the motor. However, the efficiency and energy demands of the Scripps system were such that it was not capable of unattended operation over an extended period of time.

SUMMARY OF THE INVENTION

The present invention is a system for obtaining a vertical profile of water quality in a body of water which is capable of long term unattended operation. In the system of the present invention, the winch assembly attached to the cable for deploying and retrieving the cable and the sensor in a body of water is characterized by a DC motor coupled to the drum for driving the drum to retrieve the cable, and for generating electricity during deployment of the cable in response to the torque on the motor created by the cable and the sensor during deployment; a helical reducer gear assembly for coupling mechanical power provided by the motor to the drum at a low speed and high torque; an electromagnetically released brake coupled to the motor for braking the motor when the brake is not energized; and a motor controller coupled to a battery for providing constant voltage excitation of the motor and for controlling the brake and including a device for inhibiting the motor from operating as a motor during deployment of the cable and a circuit for causing the motor to generate electricity for recharging the battery during deployment of the cable, wherein the motor speed increases during deployment only until the generated voltage equals the battery voltage, thereby causing the cable to be deployed thereafter at a speed governed by the speed-torque characteristics of the motor at the battery voltage.

It is also preferable that the drum be narrow and have large flanges and that a lead sheave for guiding the cable to and from the drum be located a sufficient distance from the drum to enable proper cable spooling on the drum.

In the preferred embodiment of the system according to the present invention, a sensor is adapted for sensing the depth of water at which said predetermined characteristics are sensed; and a control circuit is coupled to the sensor and to the motor controller for causing the motor controller to brake and stop the motor in response to sensing a predetermined depth of water.

The preferred embodiment of the present invention also includes a slow/stow detector, including a first actuator attached to the cable at a predetermined distance from the sensor and a switch positioned for contact by the first actuator when the cable is being retrieved. This switch is coupled to the motor controller for causing the motor controller to slow the motor in response to being contacted by the first actuator means. A second actuator is attached to the cable at a position which is in contact with the switch when the sensor has been retrieved from the body of water; and the motor controller is adapted for braking and stopping the motor in response to the switch being contacted by the second actuator following contact by the first actuator.

A discussion pointing out certain advantages of various features of the present invention is set forth in the Description of the Preferred Embodiment, wherein additional features of the present invention also are described.

BRIEF DESCRIPTION OF THE DRAWING

FIG. 1 shows the system of the present invention mounted on a buoy.

FIG. 7 is a cross sectional view of the electromechanical cable for lowering and retrieving the sensor and for providing data signals from the sensor taken on line 7—7 of FIG. 1.

DESCRIPTION OF THE PREFERRED EMBODIMENT

Figure 2:
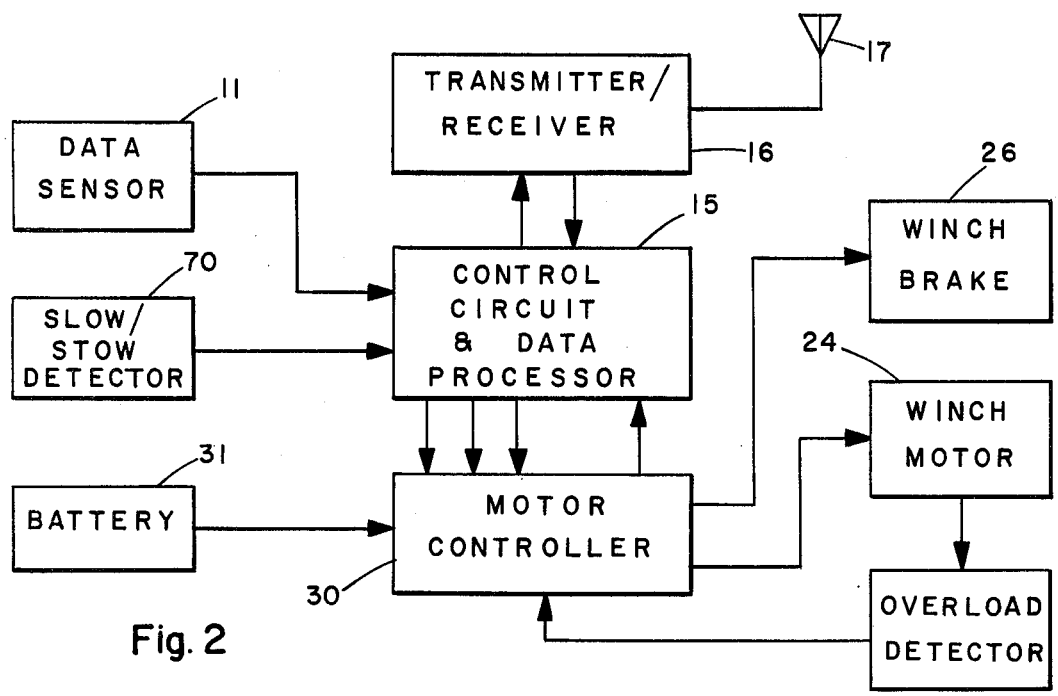
FIG. 2 is a schematic block diagram showing the interrelation of the electrical components of the system of the present invention.

A system for obtaining vertical water quality profile data mounted on an unattended buoy 10 is shown in FIG. 1. A sensor package 11 is deployed into a body of water from the buoy hull 12 by means of an electromechanical cable 13 and an automated winch 14, for measuring predetermined characteristics of water, such as temperature, depth, conductivity, pH, dissolved oxygen and transmittance (suspended solids) at a plurality of discrete levels to a given maximum depth. When data acquisition is completed, the winch 14 retrieves the sensor package 11 for stowage within the buoy 10. Profile measurement data are stored in a memory onboard the buoy 10 and may be transmitted to shore in response to receipt of a command signal.

The system is designed for operation in an ocean environment having a maximum wave height of five meters; a maximum constant current of three knots between the surface and a depth of 100 meters; a water temperature range between $-2°$ C. and $+35°$ C.; and an air temperature range between $-2°$ C. and $+40°$ C.

Referring to FIG. 2, operation of the system is controlled by a control circuit and data processor 15. Data acquired by sensor 11 are stored in a memory within the data processor. A transmitter and receiver circuit 16 is connected to the control circuit and data processor 15. Command signals detected by an antenna 17 are received by the receiver and provided to the control circuit and data processor 15. Some command signals initiate a vertical water quality profile measurement cycle and then cause the transmitter to transmit the measured data to shore. Other command signals cause the control circut and data processor 15 to cause the transmitter to transmit vertical water quality profile data previously acquired and stored in the data processor memory. Also the data processor is programmed to initiate profile measurement cycles periodically. Between profiling cycles, the system is in a standby mode, with power applied only to initialization circuitry and the data memory. The number and depth and measurements are under stored program control in the control circuit and data processor 15.

During a profile measurement cycle, the sensor 11 is deployed to a first measurement level. Upon reaching the first measurement level as indicated by the depth sensed by the data sensor 11, the winch 14 is stopped. Data are then acquired and stored in the memory. The sensor is then deployed to subsequent measurement levels for acquiring data, as described in the previous step. When data have been acquired from the final measurement level, the sensor 11 is retrieved, and power to the sensor 11 is removed. The sensor 11 is retrieved at a rate of approximately 2 feet/sec. When the sensor is within three feet of the buoy bottom 18, the retrieval rate is reduced to approximately one foot/sec. When the sensor 11 is in the buoy well 19, power is removed from the winch 14. When the measured profile data are stored in the memory and/or transmitted to shore, the systems resumes the standby mode until the next profile measurement cycle.

Figure 3:
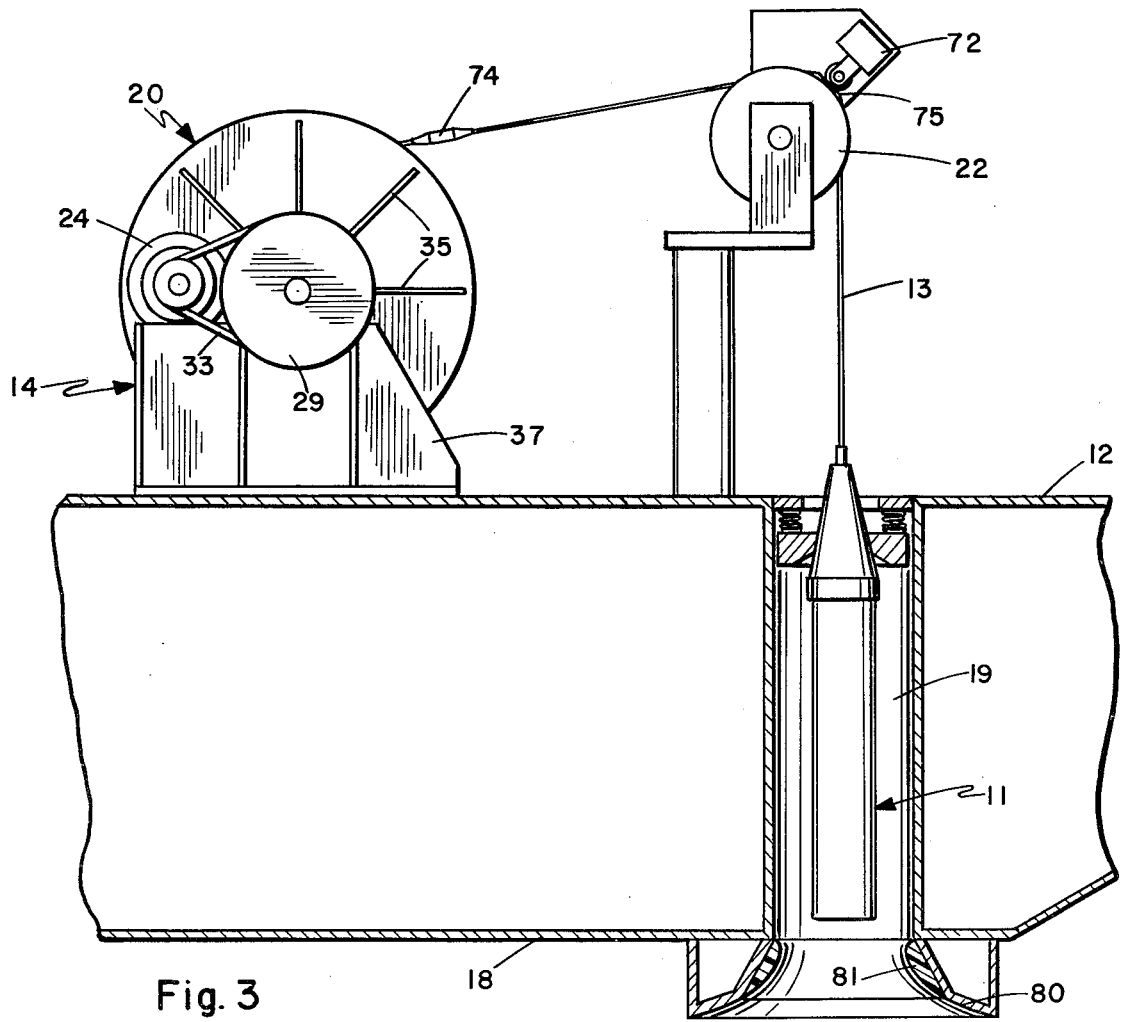
FIG. 3 is partial section view showing the winch assembly, the sensor and the slow/stow detector taken on line 3—3 of FIG. 1.
Figure 4:
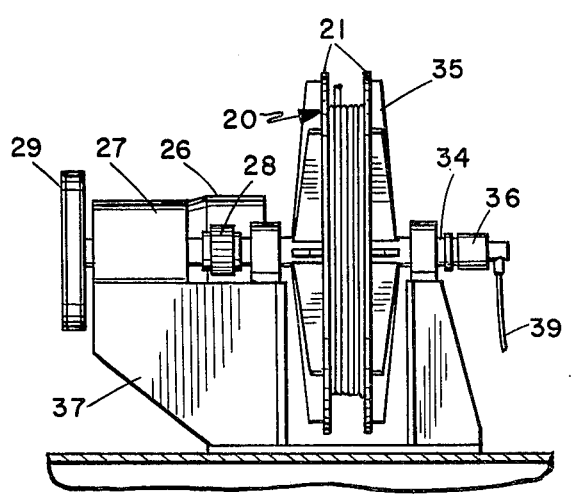
FIG. 4 is a front plan view of the winch shown in FIG. 3.
Figure 5:
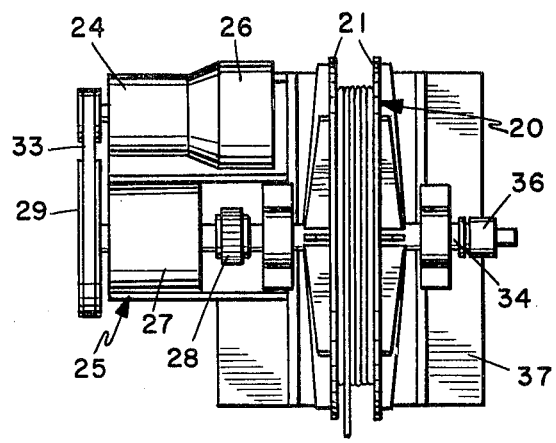
FIG. 5 is a top plan view of the winch shown in FIG. 3.
Figure 9:
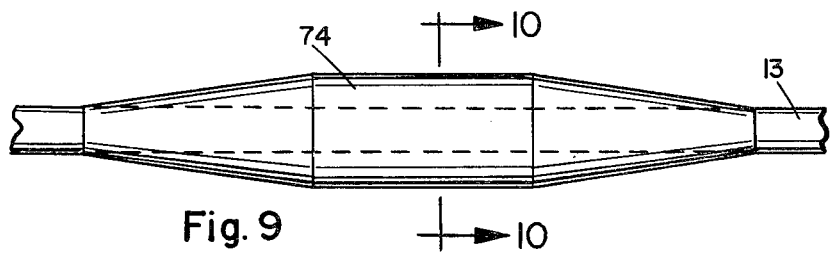
FIG. 9 is a plan view of the cable having an actuator cam attached thereto as included in the slow/stow detector of FIG. 3.
Figure 10:
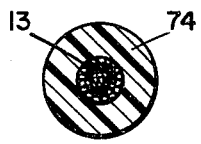
FIG. 10 is a sectional view of the cable and cam taken on line 10—10 of FIG. 9.

Referring to FIGS. 3, 4 and 5, the winch assembly 14 includes a narrow drum 20 having large flanges 21 for receiving the cable 13; a lead sheave 22 for guiding the cable 13 to and from the drum 20, and located a sufficient distance from the drum 20 to enable proper cable spooling on the drum 20; a DC motor 24 coupled to the drum 20 for driving the drum 20 to retrieve the cable 13, and for generating electricity during deployment of the cable 13 in response to the torque on the motor 24 created by the cable 13 and the sensor 11 during deployment; a helical reducer gear assembly 25 for coupling mechanical power provided by the motor 24 to the drum 20 at a low speed and high torque; and an electromagnetically released brake 26 coupled to the motor 24 for braking the motor 24 when the brake 26 is not energized. The helical reducer gear assembly 25 includes a double reduction helical gear reducer 27 coupled to the drum 20 by a shaft chain coupler 28, and a cogbelt 33 and sprockets reducer 29 for coupling the motor 24 to the double reduction helical gear reducer 27.

Referring again to FIG. 2, the system also includes a motor controller 30 for coupling the motor 24 and brake 26 to a battery 31 for providing constant voltage excitation of the motor 24 and for controlling the brake 26. The motor controller 30 inhibits the motor 24 from operating as a motor during deployment of the cable 13, and causes the motor 24 to generate electricity for recharging the battery 31 during deployment of the cable 13. The motor 24 speed increases during deployment only until the generated voltage equals the battery voltage, thereby causing the cable 13 to be deployed thereafter at a speed governed by the speed-torque characteristics of the motor 24 at the battery voltage.

During sensor deployment, the weight of the sensor 11 and cable 13 provides a torque input to the winch 14. As a result, the motor 24 is driven as a generator, thereby providing current which can be used for partial recharging of battery 31. The amount of energy generated in this manner is approximately one-quarter of the energy required during the sensor retrieval portion of the profile measurement cycle.

Figure 6:
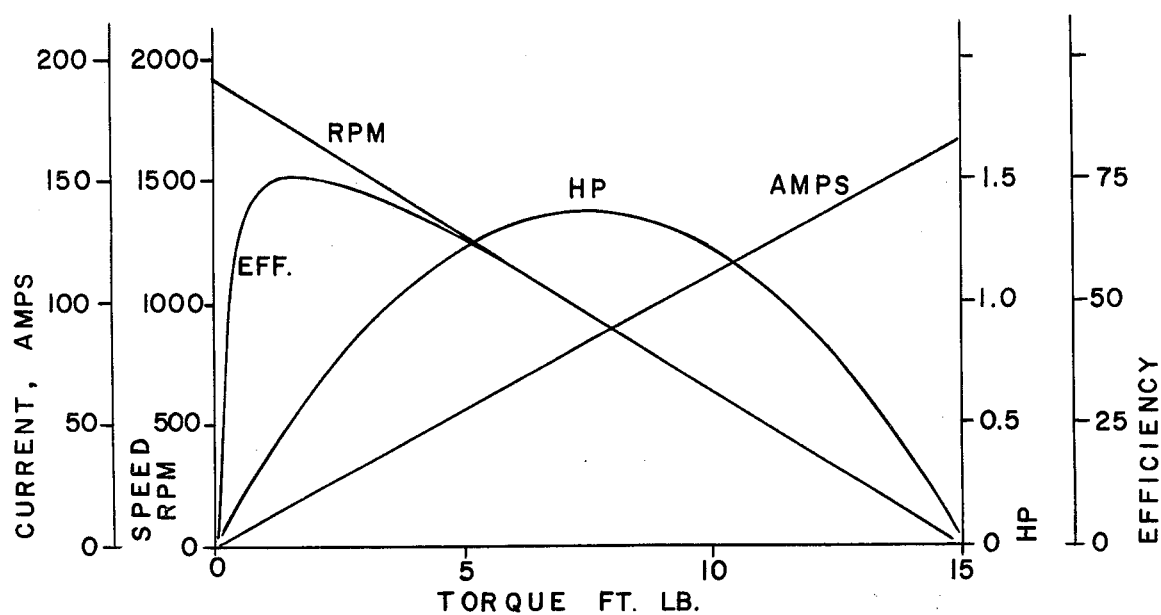
FIG. 6 is a performance curve for the motor included in the winch assembly of the preferred embodiment.
Figure 13:
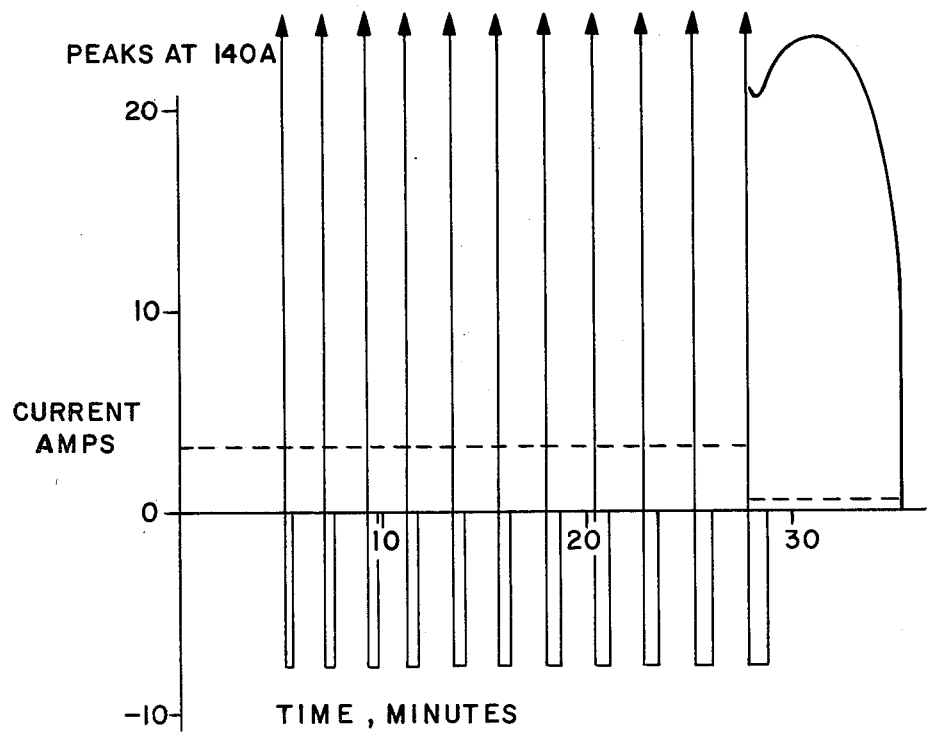
FIG. 13 shows the current-time profile for the system during a profile measurement cycle.

The motor 24 is a 24-volt permanent magnet DC motor which is totally enclosed and non-ventilated. It is normally rated at $\frac{1}{3}$ horsepower at 1800 RPM. However, for the intermittent duty cycle required of the system, it is rated at $\frac{1}{2}$ horsepower. The performance curve for the motor 24 is shown in FIG. 6. It has a stall torque of 15 lb. ft., achieves an efficiency of 74 percent at 0.50 horsepower. A DC motor is preferred over an AC motor (with a power consuming DC to AC converter) because a permanent magnet DC motor is more efficient.

The DC motor 24 is totally enclosed and non-ventilated because the enclosed feature achieves maximum environmental protection. Normally, totally enclosing a motor without forced ventilation is accompanied by power derating because of the poor heat dissipation. However, with intermittent duty required by the system of the present invention excessive heating does not result when the motor is operated at 0.5 horsepower for only several minutes. Average horsepower will vary from 0.27 to 0.53 depending on the sea current. This is ideal since, as FIG. 6 indicates, maximum efficiency is achieved close to this power range. A larger size motor will result in less efficiency and more power while a smaller motor will overheat. Thus, a motor of optimum type, voltage, enclosure, and performance characteristics has been selected.

The motor 24 is manufactured by Ohio Electric Motors in Maple Heights, Ohio and is housed in a NEMA B48 frame with a standard mounting base. A NEMA C56 face 32 is provided at the end of the motor 24 to which the brake 26 is attached. A 0.62 inch diameter shaft 34 with standard keyway is provided on both ends of the two-shafted motor 24.

The reducer assembly 27, 28, 29, 33 transmits the mechanical power supplied by the motor 24 to the winch drum 20 at a low RPM and high torque. The means selected to provide the reduction include a 34.1:1 double reduction helical gear reducer 27 rated for 0.80 input horsepower at an input speed of 600 RPM; and 3.23:1 cogbelt 33 and sprockets reducer 29. This reducer assembly 27, 28, 29, 33 provides an optimum speed reduction between the motor 24 and winch drum 20 of 100:1.

The fall-safe brake 26 (wherein application of electrical power releases brake torque and removed of power applies brake torque) uses the least power in a measurement profile cycle and provides protection for the sensor 11 should a power failure occur.

The requirement for a method of securing the sensor 11 in the stowed position is simultaneously met by the high torque capability of the brake; in that the brake 26 is capable of supporting a load in excess of the sensor 11 dynamics load. Thus, the requirement of a separate sensor 11 locking mechanism is eliminated and increased reliability results.

The brake 26 has the following features. The housing is waterproof, fabricated from brass, and is specifically designed for marine use. The brake 26 is self-adjusting to provide a continuous dependable torque. This is especially necessary between long servicing periods. The brake 26 is a dual disc brake, and thereby provides double the wear capacity. Soft-stop linings are used to cushion the braking load during activation. Infrequent servicing results from the self-adjusting feature in conjunction with the high brake life. Unlike other brakes, this brake 26 need not be completely disassembled to replace the brake discs. After the discs are installed the brake 26 need not be adjusted because the self-adjuster automatically accomplishes this. Application of 24-volts to the brake terminals releases the brake 26 torque. A current of 21.18 amps is applied for approximately 20 msec. during the pull-out interval. Upon completion of the torque release, a lower electromagnetic force is required to hold the brake 26 in the deactivated position and a lower power consuming circuit is switched in requiring only 0.37 amps continuously until the power is released. The brake 26 is manufactured by Stearns and is their P/N 1-087-006KS-5 model with provisions to fit a NEMA 56C frame and 0.62 inch diameter keyed shaft.

The drum 20 provides spooling and termination of the electromechanical cable 13.

The optimum winch drum 20 diameter and width are 12 inches and 2.5 inches, respectively. The minimum diameter of the flanges required to contain 635 feet of cable 13 is 25 inches. A smaller drum 20 diameter would be preferred, but the minimum recommended bend diameter of the cable 13 limits this dimension to 12 inches.

A level-wind for the drum 20 was considered but decided against because of inconsistency of operation (which ultimately results in a requirement for manual supervision), the additional power required, and the reduction in reliability. Since none of the above can be tolerated on an unmanned buoy, it was decided to use a simple form of level-wind based on fleet angle. Level-wind results simply by providing a narrow angle (fleet angle) of cable feed to the drum 20. The preferred maximum fleet angle is $1\frac{1}{4}°$. The $1\frac{1}{4}°$ fleet angle requires that the lead sheave 22 be no closer to the drum 20 than 57 inches.

Experience has shown that a perfect level-wind is not attainable. Therefore, a factor of 1.25 to account for irregular cable spooling has been included in the determination of the allowable flange 21 diameter. The actual flange 21 diameter is 5 inches greater than the allowable diameter to assure adequate drum 20 capacity.

The drum 20 is driven directly by the helical gear reducer 27 through a shaft coupling 28 and is supported on both ends by sealed ball-bearing assemblies which are mounted to the winch frame.

The drum is fabricated from 5086-H32 aluminum plate and tube. This material is utilized because of its low corrosion, high strength after welding and ease of fabrication.

The drum 20 is an aluminum weldment consisting primarily of 2 circular flanges 21 welded to a narrow drum through which a tubular shaft 34 passes and is supported by bearings. Eight gussets 35 are located on the outside surface of each flange to provide stiffness with minimum weight.

The tubular shaft 34 which is welded on the center line of the flanges 21 provides a means through which the electromechanical cable 13 can terminate into a slip-ring assembly 36. The shaft 34 also provides a means of attachment to the reducer shaft coupling 28 and is the drive shaft for the drum 20, being supported by bearings on both ends. All welding is continuous to prevent moisture entrapment and corrosion. All external aluminum surfaces are sandblasted and heated and then finished with a powdered epoxy applied to the heated surfaces to provide a durable corrosion-resistant surface.

The winch frame 37 provides a common attachment for all the working components of the winch assembly. It must be rigid, durable and utilize space and weight economically.

The slip-ring assembly 36 provides a means of electrically connecting the rotating end of the electromechanical cable 13 to a fixed electrical cable 39. The slip-ring assembly is a model P/N IEL BX-8 manufactured by Instrument Engineering Co., in Austin, Texas. The housing is fabricated from passivated stainless steel and is sealed to protect all components from the marine environment. The slip-ring assembly 36 utilizes 2 beryllium copper leaf springs and 4 low-noise silver graphite contacts in each of eight 5-amp circuits.

The slip-ring assembly 36 is cantilever-mounted to the end of the drum shaft 34 by a flange and 4 bolts. Low friction within the assembly 36 eliminates any requirement for anti-rotation provisions (the weight of the cable attachment will prevent rotation). A Bendix PYGMY PT01 cable connecting plug and PT06 straight plug terminate the cables.

The bearings (not shown) which support the winch drum 20 are McGill ball bearings (2 inch bore) mounted in pillow blocks (P/N C-25-2). The bearings are sealed from the environment and a lubrication fitting is provided.

The coupling 28 for transmitting power from the helical gear reducer 27 to the drum drive shaft 34 is a Falk model 60T10, with a cover. The cover, supplied with a grease fitting, provides environmental protection and continuous lubrication to the chain. The coupling, rated at 0.75 horsepower, allows for a limited axial and angular misalignment between the reducer and the drum.

The drive shaft 34 includes an aluminum tube 34 welded to the drum 20, and transmits power from the reducer coupling 28 to the drum 20. One end of the shaft 34 is keyed to the coupling 28, while the other end is pinned to the tube with two tapered pins which assure a solid connection. Nuts threaded on the pins guarantee a continuous tight fit. The shaft is fabricated from passivated stainless steel.

All external surfaces, except those protected by the powdered epoxy finish and the contacting surfaces of moving parts (such as the timing belt and its sprokets), are painted with a two-part epoxy finish.

The electromechanical cable 13 provides electrical continuity for power to the sensor 11 and data return from the sensor 11 to the control circuit and data processor 15. The cable 13 must be capable of withstanding the static and dynamic tensile loads imposed during a measurement profile cycle. To minimize the work (energy) required during sensor 11 retrieval a 0.5 inch diameter cable 13 with the highest possible specific gravity should be used. The cable 13 is a double armored steel cable as shown in cross-section in FIG. 7. The cable has a 5/16 inch diameter and a specific gravity of approximately 5.0. In a 3 knot current, the length of cable 13 required for the sensor 11 to reach a 100 m depth is approximately 625 feet.

The double armored cable 13 contains seven tightly packed tinned copper wire electrical conductors 39 having a 0.027 inch diameter and being individually insulated with a propylene copolymer 40. The package of seven tightly packed conductors 39 is wrapped in Mylar tape 42 and cotton braid 44. The cable further includes two layers 45, 46 of high strength galvanized steel wires that are contrahelically wound. The cable has a 5000 pound breaking strength and weighs 175 pounds/1000 feet (in air). The type of cable selected (including terminations) is routinely employed in the offshore oil industry (well logging operations) and in oceanographic surveys.

Regarding corrosion protection, an overall jacket for cables reeled in and out from winches is not recommended. Flaws in the jacketing (e.g., pinholes, abrasion-related cuts) can result in localized corrosion which is greatly accelerated because of the localization. The conventional approach leaves the cable unjacketed, allowing a protective oxide to form on the surface of the strength member after exposure to the elements. Galvanized steel cables employed in this manner can be expected to retain full breaking strength during 6 months of service. From 6 months to 1 year, the breaking strength of the cable may degrade by 50 percent.

Figure 8:
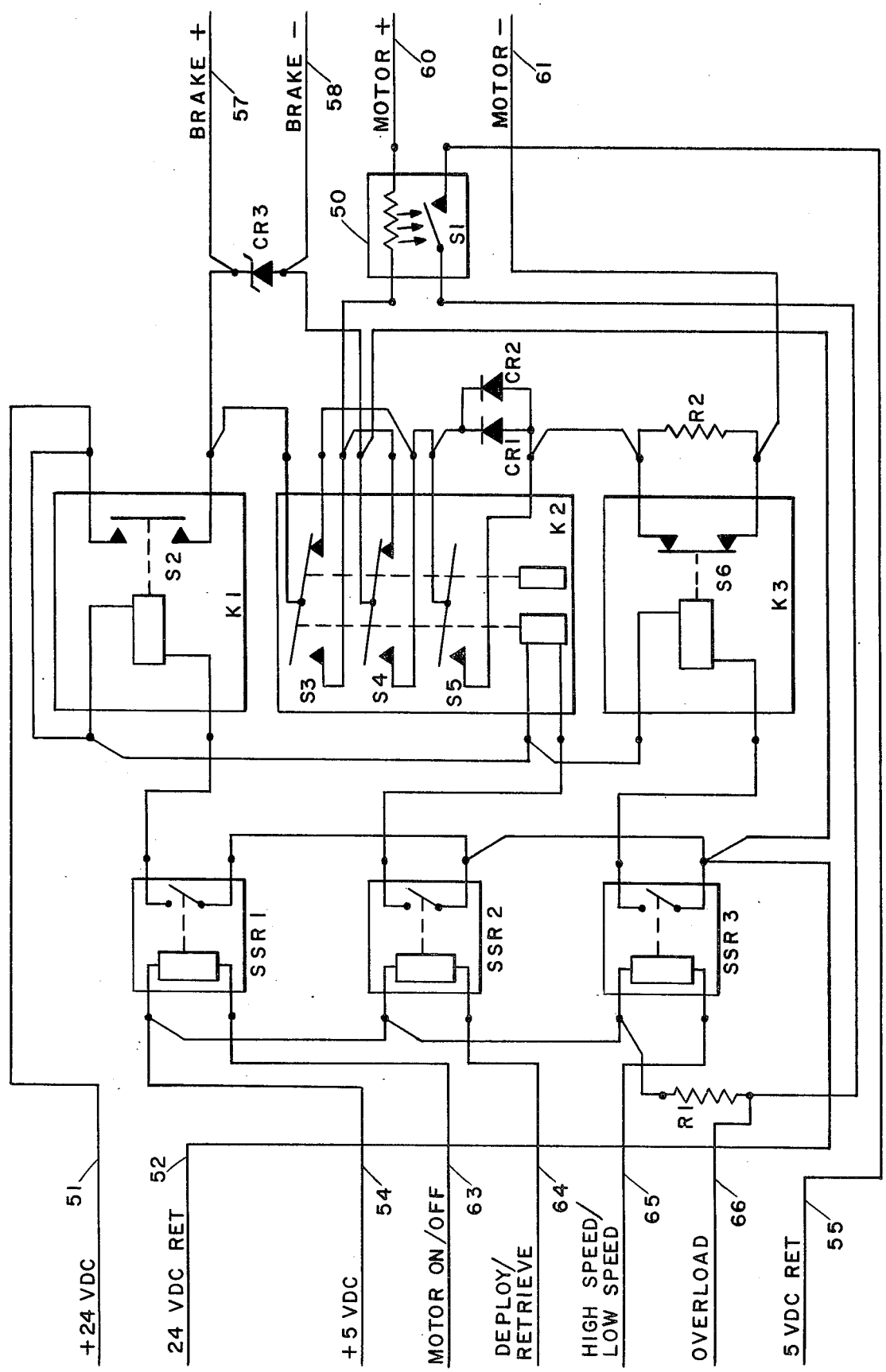
FIG. 8 is a schematic circuit diagram of the motor controller shown in FIG. 2.

Referring to FIG. 8, the motor controller 30 includes three relays K1, K2 and K3, three solid state relay drivers, SSR1, SSR2 and SSR3, resistances R1 and R2, an overload (motor stall) detector 50, diodes CR1 and CR2 and zener diodes CR3.

Lines 51 and 52 are connected to a 24 volt supply circuit which is connected to the battery 31. Line 51 provides a +24 volts DC voltage, and line 52 provides a DC voltage return line to the 24 volts supply circuit.

Lines 54 and 55 are connected to a 5 volt DC source (not shown) which is supplied from the battery 31. Line 54 provides a +5 volts DC voltage and line 55 provides a DC voltage return line to the 5 volt source.

Lines 57 and 58 are respectively connected to the positive and negative terminals of the brake 26.

Lines 60 and 61 are respectively connected to the positive and negative terminals of the motor 24.

Lines 63, 64, 65 and 66 are connected to the control circuit and data processor 15. A "motor on/off" control signal is provided to the motor controller 30 on line 63. A "deploy/retrieve" control signal is provided to the motor controller 30 on line 64. A "high speed/low speed" control signal is provided to the motor controller 30 on line 65. An overload signal is provided from the motor controller 30 on line 66.

The circuit of FIG. 8 shows the relays K1, K2 and K3 and solid state relay drivers SSR1, SSR2 and SSR3 in the state that they occupy when high level (logic "1") control signals are provided on lines 63, 64 and 65 from the control circuit and data processor 15.

The relay K1, K2 and K3 are solenoid actuated power contactor relays manufactured by ATO, Hartman Electric Manufacturing Division. The relays K1, K2 and K3 have a minimum pull-in voltage of 18 volts, and coil resistances of approximately 120 ohms. The relays are sidestable, which means that there is no center off position. The normal contact configuration without power to the coils was chosen to minimize power dissipation in the relay coils.

The relays are all rated to carry the normal motor load and inrush currents. Transient surges in relay coils, brake 26 solenoid and motor 24 armature winding inductances are all suppressed by reverse biased diodes CR1 and CR2.

The control signal lines 63, 64, 65 between the motor controller 30 and the control circuit and data processor 15 must be isolated from the circuitry of the relays K1, K2 and K3 to minimize the effects of conducted interference and preclude the possibility of damage to the control circuit and data processor 15 by reason of a malfunction in the circuitry of relays K1, K2 and K3. This isolation is accomplished by using optical isolation. The levels of the control signals on lines 63, 64 and 65 is 8 milliamps at 5 volts d.c., which is sufficient to drive the optically coupled d.c. solid state relays SSR1, SSR2 and SSR3. These relay drivers are capable of handling 5 amps in their output circuits, which are connected to the solenoids of relays K1, K2 and K3. A solid state relay driver is preferred over mechanical devices because of its inherent reliability. The solid state relay drivers SSR1, SSR2 and SSr3 draw only 15 milliamps, maximum, from the 24 volt supply when in standby operation.

The overload detector 50 is a thermally activated set of contacts which indicate when the motor is stalled. The overload detector 50 responds to the level of current in line 61 to the motor 24. Stall current is at least four times operating current. The closing of switch S1 in the overload detector 50 results in a low lever (logic "0") overload signal being provided on line 66 to the control circuit and data processor 15. The overload detector 50 is a 30 amp thermal overload switch. When the overload signal is provided on line 66, the control circuit and a data processor 15 causes the level of the signal on line 63 to go high to thereby remove power from the motor 24 in one preferred embodiment.

In another preferred embodiment, the control circuit and data processor 15 responds to a low lever overload signal on line 66 by providing a signal on line 65 that alternates between high and low levers to thereby vary the speed of the motor 24, until the stall condition passes. The latter strategy, wherein cable tension is reduced, can be effective in recovering from a mooring line entanglement situation.

A thermally activated overload detector has an inherent time delay which can vary on the order to tens of seconds, depending upon the magnitude of the overload. An overload detector having a trip point at approximately 30 amps with a 10 second time delay is believed to be adequate.

The resistance R2 is used in the low speed mode and does not dissipate power continuously. However, in a manual control mode, situations may arise in which it is desirable to run the motor for extended periods at slow speed. Consequently, the resistance R2 is large enough to allow dissipation at locked rotor current for a 50% duty cycle. A resistance R2 value of 0.5 ohms is preferred, considering the speed-torque characteristic of the motor 24. For the torque required to retrieve the sensor in a 3 knot sea current, a larger value resistance might stall the motor. With the 0.5 ohm value, the speed at which the senor 11 approaches the buoy 10 is reduced from approximately 2 feet per second to a value between 0.7 and 1.0 feet per second, depending upon the sea current.

A manual control module (not shown) may be provided to allow operation of the motor controller 30 independently of, but simultaneously with, the control circuit and data processor 15. In the manual control mode, toggle switches are used to provide the command signals on lines 63, 64 and 65 to the motor controller, an audio alarm (not shown) is connected to the overload detector 50 to indicate an overload condition.

The control signal input lines 63, 64 and 65 are respectively connected to an associated solid state d.c. relay, designated SSR1, SSR2 and SSR3. The solid state relay drivers SSR1, SSR2 and SSR3 drive the coils of the power contactor relays K1, K2 and K3 respectively. The solid state relay drivers are capable of sinking up to 5 amps, but are only required to sink a maximum of 400 milliamps for any one relay coil. The relays K2 and K3 only require 200 milliamps at 24 volts, while the relay K1 requires 400 milliamps. The 5 amp rating for the solid state relay drivers is for a 1.3 W/degree C heat sink. Without heat sink the solid state relay drivers are still rated at 3 amps at 35° C. The use of these relay drives allows some flexibility in the choice of power contactors (i.e., a large drive capability is provided) and insures that the solid state relay drivers will not be run at their limits while in normal operation. In order to use the solid state relay drivers, the manufacturer specifies that the succeeding relay coils be diode suppressed. Accordingly, relays K1, K2 and K3 include internal suppression and blocking diodes.

Diodes CR1 and CR2 are transient voltage suppressors to suppress the inductive spike associated with the motor 24 armature winding and the brake 26 solenoid winding. They will stand off 44 volts in the reverse direction, which is 20 volts above the 24 volt supply.

Resistance R2 is a 225 watt power resistor, wirewound on a tubular form. Resistance R2 reduces the speed of the motor 24 when switched into the circuit. At 100% duty cycle, the resistance R2 would dissipate less than 600 watts. Since the resistance R2 is only expected to be in the circuit once per cycle for approximately 3 seconds, no appreciable heat rise should result during normal operation. However, in the manual operation mode it may be necessary to run the motor at slow speeds for longer periods of time; hence, the resistance R2 is large enough to allow for this eventuality. The value of resistance R2 is 0.5 ohms. Should consideration be given to slowing the motor for longer periods of time (i.e., more than 3 seconds) some provision may have to made to heat-sink the resistor and/or mount it external to the box in which the remainder of the motor controller circuitry resides.

The power contactor relays K1, K2 and K3 are sidestable Hartman relays whose characteristics have been matched to the expected operating currents and cycles. In particular, the power on/off relay K1 must have a long expected life since it will be operated ten times more often than the other two relays K2 and K3. The contactor chosen for relay K1 has an expected life of 200,000 cycles, minimum.

At the high currents in the motor 24 during the motor start, the effect of relay contact resistances, internal battery impedance, brake solenoid resistance, and cable length become important to insure that the brake 26 relay solenoid is held in as the battery voltage drops under the heavy load. For this reason, it is necessary to specify the electrical cable lengths between the battery 31 and the motor controller, and between the motor controller and the motor 24 and brake 26. The effects of all of the above factors have been taken into account when specifying the battery 31 and contactors. It is assumed that no smaller than 8 AWG copper wire is used, and that no more than 10 feet of electrical cable is required between the battery 31 and the motor controller 30, and no more than 25 feet of cabling exists between the motor controller 30 and either the motor 24 or the brake 26.

A slow/stow detector 70 provides signals to the control circuit and data processor 15 when the sensor 11 is within 3 feet of the hull bottom 18 and when the sensor 11 is safely stowed within the well 19. The indication of sensor proximity to the buoy hull bottom 18 is used to initiate a slowing of the sensor 11 retrievel rate to ensure safe entry into the buoy well 19. The stow indication signifies that the sensor 11 is indeed safely within the buoy well 19 and that winch motor 24 excitation can be removed. The 3 foot proximity criterion is based on system inertia consideration. However, the actual distance is not critical, provided that sensor 11 speed is reduced prior to entry into the buoy well 19.

Referring to FIGS. 3, 9, 10, 11 and 12, rubber switch actuator cams 74, 75 are molded to the cable 13 at appropriate up-cable distances from the sensor 11. A limit switch 72 is mounted on the lead sheave 22 for indicating passage of the actuator cam 74, 75 by a contact closure. The switch actuator cams 74, 75 are suitably long to account for contact bounce. During retrieval the control circuit and data processor 15 monitors the limit switch 72. After the first closure of switch 72, the retrieval rate is slowed by providing a low lever signal on line 65 to the motor controller 30 to cause resistance R2 to be connected in series with the winch motor 24 armature. Upon the second closure of switch 72, a high level signal is provided on line 63 to cause the 24 volt supply to be removed from the motor 24.

In the slow/stow detector 70, the limit switch 72 is mounted next to the lead sheave 22 over which the cable 13 is laid, immediately about the hull standpipe 19. The switch 72 is actuated by molded, cylindrical rubber "cams" 74, 75 attached to the cable 13 at positions corresponding to the positions of he sensor package 11 in the slow and the stow positions. This arrangement places a minimum length requirement on the well 19 of only 3 feet, the difference between the slow and stow positions. The winch drum 20 is at least 4 feet from the sheave 22 so that the cams 74, 75 will not wind around the drum 20. The switch 72 is actuated sequentially by the two cams 74, 75. The control circuit and data processor 15 is programmed to keep track of the switch 72 sequence in relation to the deploy/retrieve cycle in order to differentiate a "slow" signal from a "stow" signal. In addition, the control circuit and data processor 15 is programmed for a timeout if the signals do not occur in the proper sequence or within a specified time of one another. Since the sensor 11 is moving at about 1 foot per second in the slow mode just prior to full retrieval, the signals can be expected within less than 5 seconds of one another. Since the cams 74, 75 move in both directions, a roller plunger type hermetically sealed switch 72 is used. This type of switch is actuated whenever a cam 74, 75 is present. The control circuit and data processor 15 ignores signals from the slow/stow detector 70 when the motor controller 30 is in the deploy mode. The cams 74, 75 should not have more than a 25 degree angle of attack to the roller plunger 77 of the switch 72. The cam 74, 75 must hold the switch 72 in its actuated (or closed) position long enough for the contacts 78, 79 to bounce and settle, and long enough for the closure to be sensed by the control circuit and data processor 15. The actuation times depend upon the length of the cam 74, 75 and can be adjusted accordingly. The switch 72 is a hermetically sealed SPDT switch. The switch 72 is mounted at a location where the cable 13 is taut against the sheave 22.

The cams 74, 75 are made of a flexible rubber which are substantial enough to resist the abrasion against the sheave 22 and the bellmouth 80 of the buoy well 19. The bellmouth 80 includes a nylon rub block 81 to minimize the effects of the sensor 11 impacting with the hull. The well 19 is lined with copper to retard biological fouling.

The 24 volts DC source is supplied by a nickel cadmium battery in a primary/secondary type of power subsystem. A 40A-H size nickel cadmium battery pack can easily supply the peak inrush current of 140A experienced when the winch motor 24 and brake 26 are initially energized. Also, 24 volt nickel cadmium battery packs are available which have a low internal resistance (e.g., 20 milliohms), resulting in insignificant modification of the motor speed-torque characteristics.

The total energy to be generated by, or stored within, the 24 volt primary power source is determined by the energy required per profiling cycle and the number of profiling cycles expected between power subsystem replenishment intervals. The 24 volt primary power source must also include provisions for restoring the secondary source (nickel cadmium battery) to a fully charged condition between profiling cycles.

Figure 11:
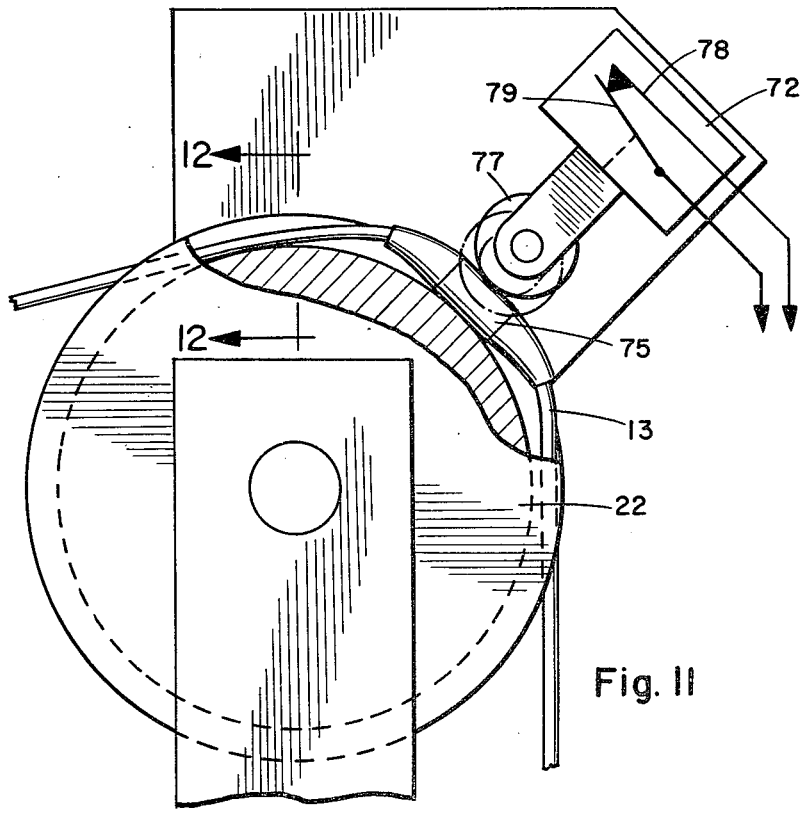
FIG. 11 is a plan view of the slow/stow detector switch and lead sheave included in the slow/stow detector and winch assembly of FIG. 3.
Figure 12:
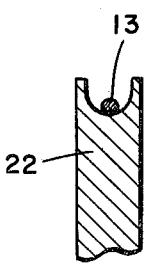
FIG. 12 is a sectional view of the lead sheave taken on line 12—12 of FIG. 11.

The current requirements for one profiling cycle in a 3 knot sea current are illustrated in FIG. 11. In a preferred profile measurement cycle data are sensed at 10 different levels up to a maximum depth of 100 meters. At each level data are sensed at the rate of one sample per second and averaged over a period of 100 seconds. After a 2 minute sensor warm-up interval, profiling begins. The current spikes represent the transient inrush which occurs when the winch motor 24 and brake 26 are excited (i.e., the sum of stalled rotor current and brake solenoid pull-in current). The negative current levels represent the current ouput of the motor 14 armature (generator action) during deployment. The period of zero current lever between spikes corresponds to sensor 11 dwell time at each measurement depth. At approximately 30 minutes into the cycle, data has been acquired at the 100 m depth and sensor retrieval begins.

With the recommended winch configuration, deployment time in a 3 knob current (including sensor dwell of 100 seconds at 10 depths) is approximately 21 minutes. The time for sensor retrieval from a depth of 100 m in a 3 knot current is approximately 9 minutes. Including time for sensor warm-up and data processing, a complete profiling cycle can be accomplished in 35 minutes or less. The average current required during retrieval is approximately 20 amperes. The net energy required from the 24 volt source for one profiling cycle in a 3 knot current is approximately 3, 9 ampere-hours. In contrast, the net energy required in a zero knot sea current condition is approximately 1.9 ampere hours.

Regarding the 5 volt source, the current required during the deployment cycle is 3 amps. During retrieval, with the sensor off, the current requirement is 0.4 amps. The total energy required from the 5 volt supply for a complete profiling cycle is approximately 1.5 ampere hours.

It should be noted that the source impedance of the 24 volt supply, together with the resistance of motor controller 30 relay contacts and system wiring affect the speed-torque characteristics of the motor 24 as shown in FIG. 6. If the combination of resistances mentioned above equals the motor 24 armature resistance the slope of the speed-torque curve doubles and the stall torque becomes 7.5 foot-pounds. For the motor 24 selected for the preferred embodiment, the armature resistance is approximately 0.15 ohms. In a 3 knot current the average motor current during sensor retrieval is approximately 20 amps.

The operation of the motor controller 30 is described with reference to FIG. 8. A low level signal is provided on line 63 when it is desired to turn the motor 24 on. A low lever signal on line 63 actuates the solid state relay driver SSR1, which in turn activates power relay K1 to close switch S2 and thereby place +24 volts DC on line 57, thus turning on the motor 24 and releasing the electromagnetic brake 26.

A low level signal is provided on line 64 when it is desired to retrieve the sensor 11. A low level signal on line 64 actuates the solid state relay driver SSR2, which in turn actuates the power relay K2 to change the positions of switches S3, S4 and S5 to make contact with the left hand contactor shown in FIG. 8. This in turn places +24 volts DC on line 60 to the positive terminal of the motor 24.

I claim:
1. A system for obtaining a vertical profile of water quality in a body of water, comprising
sensing means for sensing predetermined characteristics of water;
a cable attached to the sensing means for holding the sensing means; and a winch assembly having a drum for receiving the cable and for deploying and retrieving the cable and the sensing means in a body of water;

characterized by the winch assembly comprising a DC motor coupled to the drum for driving the drum to retrieve the cable, and for generating electricity during deployment of the cable in response to the torque on the motor created by the cable and the sensing means during said deployment;

a helical reducer gear assembly for coupling mechanical power provided by the motor to the drum at a low speed and high torque;

an electromagnetically released brake coupled to the motor for braking the motor when the brake is not energized; and a motor controller for coupling the motor and brake to a battery for providing constant voltage excitation of the motor and for controlling the brake; and including means for inhibiting the motor from operating as a motor during deployment of the cable; and for causing the motor to generate electricity for recharging said battery during deployment of the cable, wherein the motor speed increases during said deployment only until the generated voltage equals the battery voltage, thereby causing the cable to be deployed thereafter at a speed governed by the speed-torque characteristics of the motor at the battery voltage.

2. The system according to claim 1, wherein the sensing means are adapted for sensing the depth of water at which said predetermined characteristics are sensed; and further comprising means coupled to the sensing means and to the motor controller for causing the motor controller to brake and stop the motor in response to sensing a predetermined depth of water.

3. A system according to claim 1, further comprising actuator means attached to the cable at a predetermined distance from the sensing means; and switch means positioned for contact by the actuator means when the cable is being retrieved, and coupled to the motor controller for causing the motor controller to slow the motor in response to being contacted by the actuator means.

4. A system according to claim 3, further comprising second actuator means attached to the cable at a position which is in contact with the switch means when the sensing means has been retrieved from said body of water; and wherein the motor controller is adapted for braking and stopping the motor in response to the switch means being contacted by the second actuator means following contact by the first mentioned actuator means.

5. A system according to claim 1, wherein the motor is non-ventilated to provide protection from the environment.

6. A system according to claim 1, wherein the helical reducer gear assembly comprises a double reduction helical gear reducer coupled to the drum; and a cogbelt and sprockets reducer for coupling the motor to the double reduction helical gear reducer.

7. A system according to claim 6, wherein the helical reducer gear assembly provides a speed reduction between the motor and the drum of approximately 100:1.

8. A system according to claim 1, further comprising means for sensing when the motor is overloaded coupled to the motor controller;

wherein the motor control is adapted for stopping the motor in response to sensing that the motor is overloaded.

9. A system according to claim 1, further comprising means for sensing when the motor is overloaded coupled to the motor controller;

wherein the motor controller is adapted for varying the speed of the motor to vary the tension in the cable in response to sensing that the motor is overloaded until the overload condition ceases to be sensed.

10. A system for obtaining a vertical profile of water quality in a body of water comprising sensing means for sensing predetermined characteristics of water;

a cable attached to the sensing means for holding the sensing means; and a winch assembly attached to the cable for deploying and retrieving the cable and the sensing means in a body of water, wherein the winch assembly comprises a narrow drum having large flanges for receiving the cable;

a lead sheave for guiding the cable to and from the drum, and located a sufficient distance from the drum to enable proper cable spooling on the drum;

a DC motor coupled to the drum for driving the drum to retrieve the cable, and for generating electricity during deployment of the cable in response to the torque on the motor created by the cable and the sensing means during said deployment;

a helical reducer gear assembly for coupling mechanical power provided by the motor to the drum at a low speed and high torque;

an electromagnetically released brake coupled to the motor for braking the motor when the brake is not energized; and a motor controller for coupling the motor and brake to a battery for providing constant voltage excitation of the motor and for controlling the brake; and including means for inhibiting the motor from operating as a motor during deployment of the cable; and for causing the motor to generate electricity for recharging said battery during deployment of the cable, wherein the motor speed increases during said deployment only until the generated voltage equals the battery voltage, thereby causing the cable to be deployed thereafter at a speed governed by the speed-torque characteristics of the motor at the battery voltage;

wherein the cable is double armored electromechanical cable having a specific gravity of approximately 5 and a diameter of approximately 5/16 inch, the drum diameter is approximately 12 inches, and the lead sheave diameter is approximately 12 inches.

11. A system according to claim 10, wherein the drum has a width of approximately 2.5 inches and the lead sheave is located at least 57 inches from the drum for providing a maximum fleet angle of 1.25° to enable proper cable spooling on the drum.

12. A system for obtaining a vertical profile of water quality in a body of water comprising sensing means for sensing predetermined characteristics of water;

a cable attached to the sensing means for holding the sensing means; and a winch assembly attached to the cable for deploying and retrieving the cable and the sensing means in a body of water, wherein the winch assembly comprises a narrow drum having large flanges for receiving the cable;

a lead sheave for guiding the cable to and from the drum, and located a sufficient distance from the drum to enable proper cable spooling on the drum;

a DC motor coupled to the drum for driving the drum to retrieve the cable, and for generating electicity during deployment of the cable in response to the torque on the motor created by the cable and the sensing means during said deployment;

a helical reducer gear assembly for coupling mechanical power provided by the motor to the drum at a low speed and high torque;

an electromagnetically released brake coupled to the motor for braking the motor when the brake is not energized; and a motor controller for coupling the motor and brake to a battery for providing constant voltage excitation of the motor and for controlling the brake; and including means for inhibiting the motor from operating as a motor during deployment of the cable; and for causing the motor to generate electricity for recharging said battery during deployment of the cable, wherein the motor speed increases during said deployment only until the generated voltage equals the battery voltage, thereby causing the cable to be deployed thereafter at a speed governed by the speed-torque characteristics of the motor at the battery voltage;

wherein the drum has a width of approximately 2.5 inches and the lead sheave is located at least 57 inches from the drum for providing a maximum fleet angle of 1.25° to enable proper cable spooling on the drum.

13. A system for obtaining a vertical profile of water quality in a body of water, comprising sensing means for sensing predetermined characteristics of water;

a cable attached to the sensing means for holding the sensing means;

a winch assembly having a drum for receiving the cable and for deploying and retrieving the cable and the sensing means in a body of water;

a motor coupled to the drum for driving the drum to retrieve the cable; and a motor controller coupled to the motor for controlling the motor;

characterized by first actuator means attached to the cable at a predetermined distance from the sensing means; and switch means positioned for contact by the first actuator means when the cable is being retrieved, and coupled to the motor controller for causing the motor controller to slow the motor in response to being contacted by the first actuator means; and second actuator means attached to the cable at a position which is in contact with the switch means when the sensing means has been retrieved from said body of water; and wherein the motor controller is adapted for stopping the motor in response to the switch means being contacted by the second actuator means following contact by the first mentioned actuator means.

14. A system for obtaining a vertical profile of water quality in a body of water, comprising sensing means for sensing predetermined characteristics of water;

a cable attached to the sensing means for holding the sensing means;

a winch assembly having a drum for receiving the cable and for deploying and retrieving the cable and the sensing means in a body of water, a motor coupled to the drum for driving the drum to retrieve the cable; and a motor controller coupled to the motor for controlling the motor;

characterized by the sensing means being adapted for sensing the depth of water at which said predetermined characteristics are sensed; and by further comprising means coupled to the sensing means and to the motor controller for causing the motor controller to stop the motor in response to sensing a predetermined depth of water.

15. For use in a system for obtaining a vertical profile of water quality in a body of water, wherein a sensing means for sensing predetermined characteristics of water is attached to a cable which is attached to a winch assembly having a drum for receiving the cable and for deploying and retrieving the cable and the sensing means in a body of water; a winch assembly comprising a DC motor coupled to the drum for driving the drum to retrieve and cable, and for generating electricity during deployment of said cable in response to the torque on the motor created by said cable and said sensing means during said deployment;

a helical reducer gear assembly for coupling mechanical power provided by the motor to the drum at a low speed and high torque;

an electromagnetically released brake coupled to the motor for braking the motor when the brake is not energized;

a motor controller for coupling the motor and brake to a battery for providing constant voltage excitation of the motor and for controlling the brake; and including means for inhibiting the motor from operating as a motor during deployment of said cable; and for causing the motor to generate electricity for recharging said battery during deployment of said cable, wherein the motor speed increases during said deployment only until the generated voltage equals the battery voltage, thereby causing the cable to be deployed thereafter at a speed governed by the speed-torque characteristics of the motor at the battery voltage.

* * * * *